United States Patent
Locke

(10) Patent No.: US 11,224,543 B2
(45) Date of Patent: Jan. 18, 2022

(54) NEGATIVE PRESSURE WOUND THERAPY SYSTEM WITH DETECTION OF FULL ABSORBENT DRESSING

(71) Applicant: KCI LICENSING, INC., San Antonio, TX (US)

(72) Inventor: Christopher B. Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 342 days.

(21) Appl. No.: 16/393,437

(22) Filed: Apr. 24, 2019

(65) Prior Publication Data

US 2019/0336344 A1   Nov. 7, 2019

Related U.S. Application Data

(60) Provisional application No. 62/666,461, filed on May 3, 2018.

(51) Int. Cl.
*A61F 13/00* (2006.01)
*A61M 1/00* (2006.01)
(Continued)

(52) U.S. Cl.
CPC ......... *A61F 13/00068* (2013.01); *A61M 1/90* (2021.05); *A61B 5/445* (2013.01);
(Continued)

(58) Field of Classification Search
CPC ...... A61F 13/00068; A61F 2013/00174; A61F 2013/8494; A61F 13/00029; A61M 1/90;
(Continued)

(56) References Cited

U.S. PATENT DOCUMENTS 1,355,846 A   10/1920   Rannells
2,547,758 A   4/1951   Keeling
(Continued)

FOREIGN PATENT DOCUMENTS

AU   550575 B2   3/1986
AU   745271 B2   3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Nicholas J Weiss
*Assistant Examiner* — Seth Han

(57) ABSTRACT

A method for detecting a state of a dressing includes measuring air pressure within a tube. The tube provides airflow between a pump device and the dressing. The method also includes determining whether the air pressure differs from a pressure setpoint by more than a preset limit, and running the pump to cause the air pressure to approach the pressure setpoint. In response to a determination that the air pressure does not differ from the pressure setpoint by more than the preset limit, the method also includes determining a duration of time since a last running of the pump, determining whether the duration of time since the last running of the pump exceeds a threshold duration, and, in response to a determination that the duration of time since the last running of the pump exceeds the threshold duration, generating an alert that indicates that the dressing is full.

8 Claims, 10 Drawing Sheets

(51) Int. Cl.
*A61B 5/00* (2006.01)
*A61F 13/84* (2006.01)
*A61F 13/40* (2006.01)

(52) U.S. Cl.
CPC .............. *A61F 2013/00174* (2013.01); *A61F 2013/8494* (2013.01); *A61M 35/006* (2013.01); *A61M 2205/3337* (2013.01); *A61M 2205/3344* (2013.01)

(58) Field of Classification Search
CPC .. A61M 2205/3337; A61M 2205/3344; A61M 1/73; A61M 1/982
USPC .......................................................... 604/319
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0227969 A1* | 9/2009 | Jaeb ................. A61F 13/00068 604/313 |
| 2014/0276491 A1* | 9/2014 | Luckemeyer ........... A61M 1/90 604/319 |
| 2016/0166781 A1* | 6/2016 | Sarangapani ....... A61M 1/0023 604/23 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |

(56) References Cited

FOREIGN PATENT DOCUMENTS

| WO | 99/13793 A1 | 3/1999 |
|---|---|---|
| WO | WO-2011/135287 A1 | 11/2011 |
| WO | WO-2012/141999 A1 | 10/2012 |
| WO | WO-2018/013242 A1 | 1/2018 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion in International Application No. PCT/US2019/028920, dated Nov. 8, 2019 (21 pages).

* cited by examiner

NEGATIVE PRESSURE WOUND THERAPY SYSTEM WITH DETECTION OF FULL ABSORBENT DRESSING

CROSS-REFERENCE TO RELATED APPLICATIONS

This application claims the benefit of priority to U.S. Provisional Application No. 62/666,461, filed on May 3, 2018, which is incorporated herein by reference in its entirety.

BACKGROUND

The present disclosure relates generally to wound therapy systems and devices, and more particularly to absorbent dressings for use with negative pressure wound therapy.

Negative pressure wound therapy (NPWT) is a type of wound therapy that involves applying negative pressure (relative to atmospheric pressure) to a wound site to promote wound healing. Typically, a dressing sealed over a wound site is connected to a pump that pumps air out of the wound site and dressing to provide a negative pressure at the wound site. Some NPWT systems include a dressing with an absorbent layer that absorbs exudate from the wound site. In many cases, the absorbent layer has a maximum capacity beyond which the absorbent layer can no longer absorb exudate from the wound. When the absorbent layer reaches its maximum capacity, the dressing is said to be "full."

Therefore, systems and methods for full dressing detection may be beneficial.

SUMMARY

One embodiment of the of the present disclosure is a dressing. The dressing includes a drape sealable over a wound bed, an absorbent layer coupled to the drape and configured to absorb fluid from the wound bed, and a manifold layer abutting the absorbent layer. The manifold layer allows the flow of air and fluid therethrough, and the absorbent layer is positioned between the manifold layer and the drape. The dressing also includes a first opening extending through the drape, a first conduit extending though the absorbent layer and pneumatically communicable with the first opening and the manifold layer, a first filter positioned between the first opening and the first conduit, and a connection pad positioned on the drape at the first opening. The connection pad is configured to couple a tube to the dressing in pneumatic communication with the first opening. The tube is coupled to a pump that provides a negative pressure to the wound bed. The dressing also includes a second opening extending through the drape that allows an airflow from the second opening to the tube via the manifold layer. The absorbent layer is configured to swell to block the airflow from the second opening to the tube when the absorbent layer is full of fluid.

In some embodiments, the pump is configured to detect that the absorbent layer is full of fluid by determining that the airflow from the second opening to the tube is blocked. In some embodiments, the dressing also includes a second conduit extending through the absorbent layer and pneumatically communicable with the second opening and the manifold layer. In some embodiments, the dressing also includes a second filter positioned between the second opening and the second conduit.

In some embodiments, the first filter is positioned between the second opening and the second conduit. In some embodiments, the second opening is aligned with a channel extending through the connection pad. In some embodiments, the second opening is aligned with the first conduit and the first filter. In some embodiments, the dressing also includes a perforated silicon layer abutting the manifold layer.

Another implementation of the present disclosure is a method for detecting a state of a dressing. The method includes measuring air pressure within a tube. The tube provides airflow between a pump device and the dressing. The method also includes determining whether the air pressure differs from a pressure setpoint by more than a preset limit, and, in response to a determination that the air pressure differs from the pressure setpoint by more than the preset limit, running the pump to cause the air pressure to approach the pressure setpoint. In response to a determination that the air pressure does not differ from the pressure setpoint by more than the preset limit, the method also includes determining a duration of time since a last running of the pump, determining whether the duration of time since the last running of the pump exceeds a threshold duration, and, in response to a determination that the duration of time since the last running of the pump exceeds the threshold duration, generating an alert that indicates that the dressing is full.

In some embodiments of the method, the dressing includes a drape sealable over a wound bed, an absorbent layer coupled to the drape and configured to absorb fluid from the wound bed, and a manifold layer abutting the absorbent layer. The manifold layer allows the flow of air and fluid therethrough, and the absorbent layer is positioned between the manifold layer and the drape. The dressing also includes a first opening extending through the drape, a first conduit extending though the absorbent layer and pneumatically communicable with the first opening and the manifold layer, a first filter positioned between the first opening and the first conduit, and a connection pad positioned on the drape at the first opening. The connection pad is configured to couple a tube to the dressing in pneumatic communication with the first opening. The tube is coupled to a pump that provides a negative pressure to the wound bed. The dressing also includes a second opening extending through the drape that allows an airflow from the second opening to the tube via the manifold layer. The absorbent layer is configured to swell to block the airflow from the second opening to the tube when the absorbent layer is full of fluid.

Another implementation of the present disclosure is a dressing. The dressing includes a drape sealable over a wound bed, an absorbent layer coupled to the drape and configured to absorb fluid from the wound bed, and a first manifold layer abutting the absorbent layer. The first manifold layer allows the flow of air and fluid therethrough, and the absorbent layer is positioned between the first manifold layer and the drape. The dressing also includes a first opening extending through the drape, a first conduit extending though the absorbent layer and pneumatically communicable with the first opening and the manifold layer, and a connection pad positioned on the drape at the first opening. The connection pad is configured to couple a tube to the dressing in pneumatic communication with the first opening. The tube is coupled to a pump that provides a negative pressure to the wound bed. The dressing also includes a second manifold layer positioned between the absorbent layer and the drape. The second manifold layer allows the flow of air therethrough. A plurality of perforations extend through the absorbent layer and allow airflow between the first manifold layer and the second manifold layer. The dressing also includes a second opening extending through the drape and aligned with the second manifold layer, and a sensing port pneumatically communicable with the second opening. The sensing port facilitating measurement of a pressure of the second manifold layer.

In some embodiments, the absorbent layer is configured to swell to close the perforations when the absorbent layer is full of fluid. In some embodiments, a difference between a pressure of the second manifold layer and a pressure of the first manifold layer indicates that the absorbent layer is full of fluid. In some embodiments, the connection pad comprises the sensing port.

Another implementation of the present disclosure is a method for detecting a state of a dressing. The method includes measuring a first pressure in a pump tube. The pump tube is pneumatically communicable with a pump and a dressing to allow the pump to create a negative pressure at the dressing. The method also includes measuring a second pressure in a sensor tube. The sensor tube is pneumatically communicable with a sensing port of the dressing. The method also includes comparing the first pressure and the second pressure to determine a pressure difference, determining whether the pressure difference is greater than a threshold difference, and in response to a determination that the pressure difference is greater than a threshold difference, generating an alert that indicates that the dressing is full.

In some embodiments of the method, the dressing includes a drape sealable over a wound bed, an absorbent layer coupled to the drape and configured to absorb fluid from the wound bed, and a first manifold layer abutting the absorbent layer. The first manifold layer allows the flow of air and fluid therethrough, and the absorbent layer is positioned between the first manifold layer and the drape. The dressing also includes a first opening extending through the drape, a first conduit extending though the absorbent layer and pneumatically communicable with the first opening and the manifold layer, and a connection pad positioned on the drape at the first opening. The connection pad is configured to couple a tube to the dressing in pneumatic communication with the first opening. The tube is coupled to a pump that provides a negative pressure to the wound bed. The dressing also includes a second manifold layer positioned between the absorbent layer and the drape. The second manifold layer allows the flow of air therethrough. A plurality of perforations extend through the absorbent layer and allow airflow between the first manifold layer and the second manifold layer. The dressing also includes a second opening extending through the drape and aligned with the second manifold layer, and a sensing port pneumatically communicable with the second opening. The sensing port facilitating measurement of a pressure of the second manifold layer.

Another implementation of the present disclosure is a negative-pressure wound therapy system. The negative-pressure wound therapy system includes a dressing that includes a drape sealable over the wound bed, an absorbent layer that absorbs fluid, and a manifold layer that provides a volume of air between the absorbent layer and the wound bed. The negative-pressure wound therapy system also includes a tube coupled to the dressing to allow airflow from the manifold layer to the tube. The airflow is restricted when the absorbent layer absorbs a threshold amount of fluid. The negative-pressure wound therapy system also includes a pump coupled to the tube and operable to provide negative pressure to the volume of air by pumping air out of the volume of air, and a therapy unit configured to detect whether the absorbent layer absorbs the threshold amount of fluid by measuring a pressure response ripple in the tube induced by noise in the pump and determining whether the pressure response ripple exceeds a limit.

In some embodiments, determining whether the pressure response ripple exceeds a limit comprises determining whether an amplitude of the pressure response ripple exceeds a threshold amplitude. In some embodiments, the pump is further configured to verify whether the absorbent layer absorbs the threshold amount of fluid by altering a drive frequency of the pump to accentuate the noise. In some embodiments, the pump is further configured to generate an alert in response to a determination that the absorbent layer absorbs the threshold amount of the fluid.

DETAILED DESCRIPTION

Negative Pressure Wound Therapy System

Figure 1:
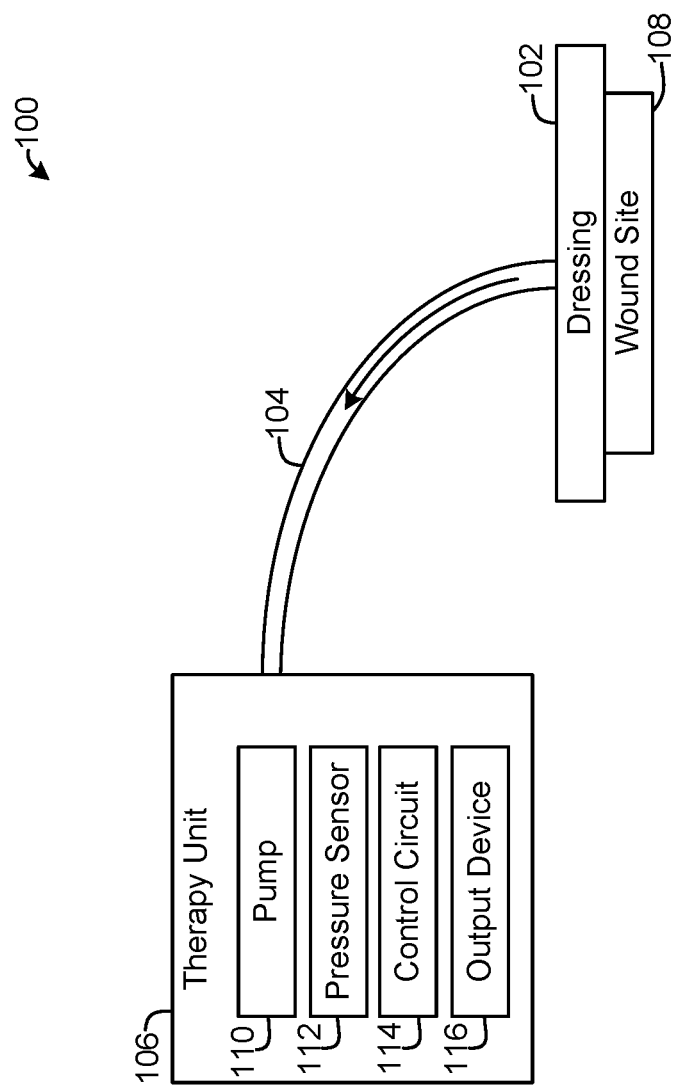
FIG. 1 is a block diagram of a negative pressure wound therapy system, according to an exemplary embodiment.

Referring to FIG. 1, a block diagram of a negative pressure wound therapy (NPWT) system 100 is shown, according to an exemplary embodiment. The NPWT system 100 provides NPWT to a patient to facilitate healing of the patient's wound and may be used in long-term care situations, for example in long-term care facilities (e.g., nursing homes, assisted living, etc.) or for outpatient or at-home treatment. The NPWT system 100 may be portable, for example such that a patient may freely move about while carrying the NPWT system 100. The NPWT system 100 includes a dressing 102 connected by a tube 104 to a therapy unit 106.

The dressing 102 is sealable over a wound site 108 (i.e., a location on a patient with an exposed laceration, burn, etc.). That is, the dressing 102 creates a substantially airtight seal around the wound site 108. Various embodiments of the dressing 102 are shown in FIGS. 2-5 and 7 and described in detail below with reference thereto. The dressing 102 is configured to provide a volume in which a negative air pressure can be applied to the wound site 108 and to absorb wound exudate from the wound site 108. The tube 104 is coupled to the dressing 102 and to the therapy unit 106. The tube 104 allows the flow of air between the dressing 102 and the therapy unit 106, typically from the dressing 102 towards the therapy unit 106.

The therapy unit 106 includes a pump 110 coupled to the tube 104, a pressure sensor 112 positioned in pneumatic communication with the tube 104 to measure pressure in the tube 104, a control circuit 114, and an output device 116. The pump 110 is operable to pump air out of the tube 104 and the dressing 102 to create a negative pressure in the tube 104 and at the wound site 108 sealed under the dressing 102. That is, the pump 110 pumps air out of a space at the wound site 108 defined by the dressing 102 to maintain the air pressure in that space below atmospheric pressure. The pump 110 is controlled by the control circuit 114 as described below. In some embodiments, the pump 110 operates with a pump cycle that creates a noise ripple in the amount of air pumped through the pump 110.

The pressure sensor 112 measures the air pressure in the tube 104 as created by the pump 110. Because the tube 104 is pneumatically communicable with the dressing 102 at the wound site 108, the pressure sensor 112 senses the air pressure at the dressing 102. That is, when the pump 110 operates to create a negative pressure in the tube 104 and at the dressing 102, the pressure sensor 112 measures that negative air pressure. In some embodiments, the therapy unit 106 includes a second pressure sensor that senses the pressure in a second tube pneumatically coupled to a sensing port on the dressing 102, for example described with reference to FIGS. 7-8. The pressure sensor 112 (and, in some embodiments, the second pressure sensor) provide air pressure measurements to the control circuit 114.

The control circuit 114 receives air pressure measurements from the pressure sensor 112 and generates controls for the pump 110 based on the air the pressure measurements. In some embodiments, the control circuit 114 generates controls for the pump 110 to cause the pump to operate to maintain the air pressure measured by the pressure sensor 112 at or around an air pressure setpoint (i.e., a desired negative pressure for the wound site 108). For example, the control circuit 114 may determine whether an air pressure measurement deviates from the air pressure setpoint by more than an acceptable margin, and, if so, generate a control signal that causes the pump 110 to pump out air. The control circuit 114 may then determine when the air pressure measurements return to the air pressure setpoint and generate a control signal to stop operation of the pump 110. The control circuit 114 may thereby turn the pump 110 on and off as needed to maintain a desired air pressure at the dressing 102 (i.e., at the wound site 108).

The control circuit 114 is also configured to determine when the dressing 102 is full of fluid. Various methods executable by the control circuit 114 for determining when the dressing 102 is full are illustrated in FIGS. 6 and 8-10 and described in detail with reference thereto. Various embodiments of dressing 102 to facilitate determinations of whether the dressing 102 is full are shown in FIGS. 2-5 and 7. When the control circuit 114 determines that the dressing 102 is full, the control circuit 114 transmits an indication that the dressing 102 is full to the output device 116.

The output device 116 receives the indication that the dressing 102 is full from the control circuit 114 and, in response, generates an output that alerts a user that the dressing 102 is full. The output device 116 may include any device suitable for providing such an alert to a user. For example, the output device 116 may include one or more lights that turn on, turn off, blink, change color, etc. to indicate that the dressing 102 is full. As another example, the output device 116 may include a speaker that generates a noise (e.g., beep, tone, ring, message, song) that indicates that the dressing 102 is full. As another example, the output device 116 includes a screen that displays a message indicating that the dressing 102 is full. In other examples, the output device 116 includes a network interface configured to transmit a signal over a network (e.g., WiFi, Bluetooth, cellular) to one or more user electronic devices (e.g., cellphones, smartphones, tablets, personal computers) and/or to a provider computing system (e.g., a nurse-call system, an electronic health record). A user or healthcare provider may then receive an alert that the dressing 102 is full via a user electronic device (e.g., an email, a text message, a push notification). All such examples and combinations thereof are included in the scope of the present disclosure.

Figure 2:
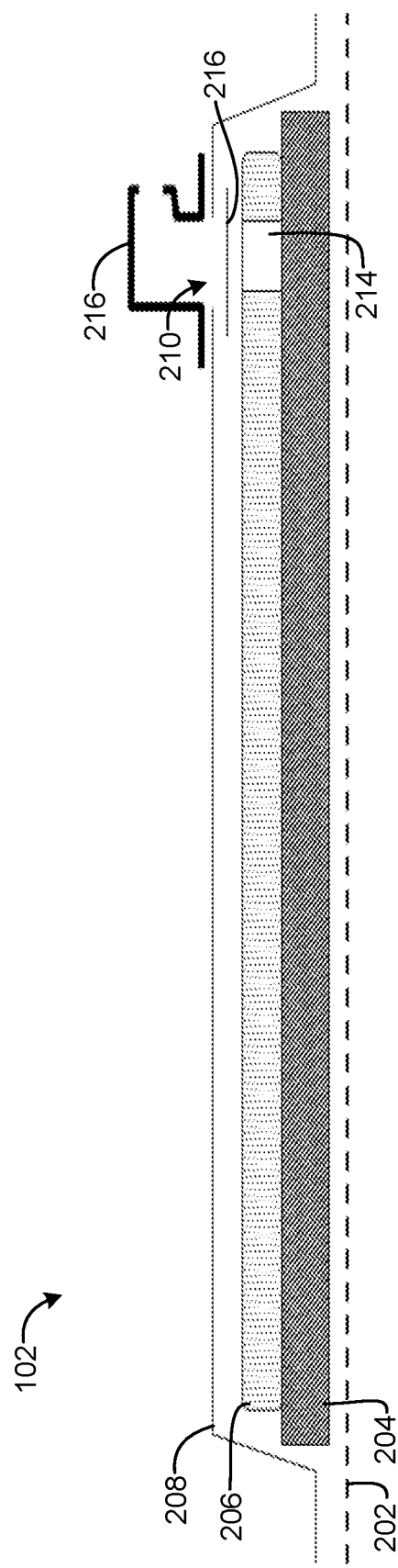
FIG. 2 is an illustration of a first dressing for use with the negative pressure wound therapy system of FIG. 1, according to an exemplary embodiment.

Referring now to FIG. 2, the dressing 102 is shown according to one exemplary embodiment. The dressing 102 includes multiple layers, including a perforated silicone layer 202, a manifold layer 204 positioned along the perforated silicone layer 202, an absorbent layer 206 positioned along the manifold layer 204, and a drape 208 positioned along the absorbent layer 206. The perforated silicone layer 202 is configured to abut the wound site 108 when the dressing 102 is in use. The perforated silicone layer 202 is perforated to allow the flow of air and fluid therethrough. The silicone layer 202 allows the dressing 102 to contact the wound site 108 and to be safely removed from the wound site 108 without damaging tissue at the wound site 108.

The manifold layer 204 is positioned along the silicone layer 202 such that the silicone layer 202 is between the manifold layer 204 and the wound site 108 when the dressing 102 is in use. The manifold layer 204 is made of a three-dimensional textile or other three-dimensional material that provides a structure through which air and fluid can flow. Accordingly, the manifold layer 204 contains a volume of air. The manifold layer 204 may substantially maintain its structure when the air contained therein is at a negative pressure relative to atmospheric pressure. That is, the manifold layer 204 may maintain a substantially constant volume. Because air flows freely through the silicone layer 202 between the wound site 108 and the manifold layer 204, the air pressure in the manifold layer 204 is substantially equivalent to the air pressure of the wound site 108. Accordingly, negative pressure is applied to the wound site 108 when the manifold layer 204 is at a negative pressure.

The absorbent layer 206 is positioned along the manifold layer 204 such that the manifold layer 204 is between the absorbent layer 206 and the silicone layer 202. That is, the absorbent layer 206 is separated from the wound site 108 by the manifold layer 204 and the silicone layer 202. The absorbent layer 206 is configured to absorb fluid from the wound bed. When the absorbent layer 206 absorbs fluid, the absorbent layer 206 swells (i.e., increases in volume).

The drape 208 is positioned along the absorbent layer 206 and defines an exterior surface of the dressing 102. The drape 208 is sealable over the wound site 108, as well as over the silicone layer 202, the manifold layer 204, and the absorbent layer 206. That is, the drape 208 may be coupled to the patient around the wound site 108 to secure the silicone layer 202, the manifold layer 204, and the absorbent layer 206 to the wound site 108. When sealed to the wound site 108, the drape 208 may be substantially air-tight, such that a substantially air tight volume is created between the drape 208 and the wound site 108. The silicone layer 202, the manifold layer 204, and the absorbent layer 206 are located in this substantially air-tight volume.

A first opening 210 extends through the drape 208 and allows air to flow through the drape 208. The first opening 210 may be a hole, a group of perforations, or some other type of opening that allows airflow through the drape 208. A first conduit 214 extends through the absorbent layer 206 and is aligned with the first opening 210. The first conduit 214 thereby allows air to flow between the first opening 210 and the manifold layer 204. The first conduit 214 may be a hole, a group of perforations, or some other type of opening that allows airflow through the absorbent layer 206. A filter 212 is positioned between the first opening 210 and the first conduit 214.

A connection pad 216 is coupled to the drape 208 at the first opening 210 (i.e., surrounding the first opening 210). The connection pad 216 is configured to couple the tube 104 to the dressing 102 in pneumatic communication with the first opening 210, and, accordingly, with the first conduit 214 and the manifold layer 204. The tube 104 is also coupled to the pump 110. The pump 110 pumps air out of the tube 104, which draws air out of the manifold layer 204 via the first conduit 214 and the first opening 210. A negative pressure is thereby established in the manifold layer 204 at the wound site 108.

As mentioned above, the absorbent layer 206 swells when the absorbent layer 206 absorbs fluid. When the absorbent layer 206 swells, airflow through the first conduit 214 may be restricted. In some cases, the first conduit 214 and the absorbent layer 206 are configured such that when the absorbent layer 206 is full (i.e., the absorbent layer 206 cannot absorb substantially more fluid) the first conduit 214 is blocked by swelling of the absorbent layer 206 and airflow through the first conduit 214 is prevented.

Dressings with Expected Leak Rates for Full Dressing Detection

Figure 3:
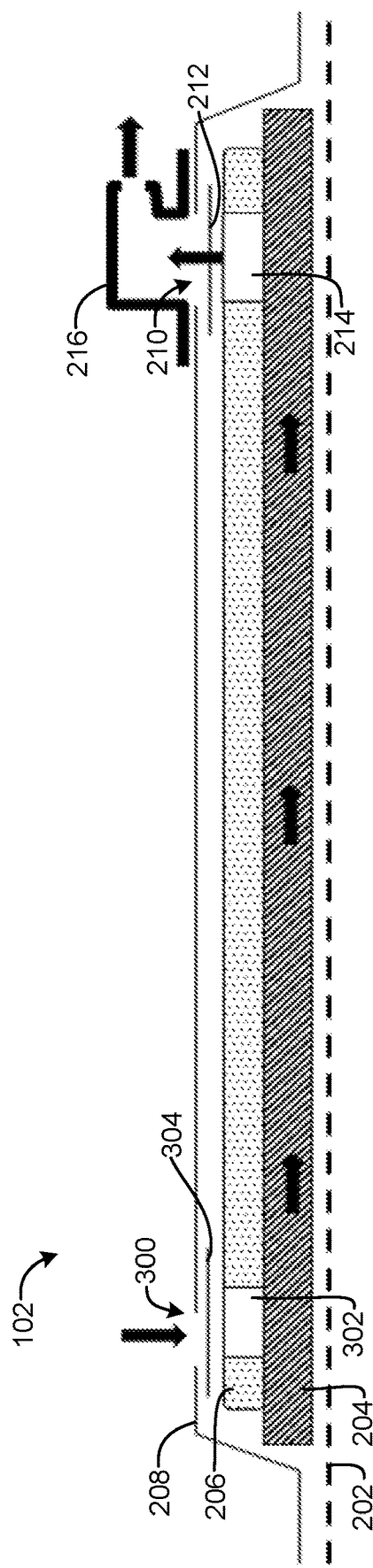
FIG. 3 is an illustration of a second dressing for use with the negative pressure wound therapy system of FIG. 1, according to an exemplary embodiment.

Referring now to FIG. 3, another embodiment of the dressing 102 is shown, according to an exemplary embodiment. As in FIG. 2, the dressing 102 includes a perforated silicone layer 202, a manifold layer 204 positioned along the perforated silicone layer 202, an absorbent layer 206 positioned along the manifold layer 204, and a drape 208 positioned along the absorbent layer 206. A first opening 210 extends through the drape 208 and is aligned with a first conduit 214. A filter 212 is positioned between the first opening 210 and the first conduit 214, and a connection pad 216 is positioned at the first opening 210 to couple the tube 104 to the drape 208 in pneumatic communication with the first opening 210, the first conduit 214 and the manifold layer 204.

In the embodiment of FIG. 3, the dressing 102 also includes a second opening 300 that extends through the drape 208. The second opening 300 is aligned with a second conduit 302 that extends through the absorbent layer 206 and allows airflow between the second opening 300 and the manifold layer 204. The second conduit 302 may be a hole, a group of perforations, or some other type of opening that allows airflow through the absorbent layer 206. A second filter 304 is positioned between the second opening 300 and the second conduit 302. In the embodiment of FIG. 3, the second opening 300 and the second conduit 302 are positioned on an opposite end or side of the dressing 102 from the first opening 210 and the connection pad 216.

The second opening 300 and the second conduit 302 allow air to flow from the environment into the manifold layer 204, drawn in by the negative pressure maintained at the manifold layer 204 by the pump 110 via the tube 104 coupled to the connection pad 216 at the first opening 210. When the pump 110 is operating, air flows in through the second opening 300 and the second conduit 302, through the manifold layer 204, and out the first conduit 214, the first opening 210, and the connection pad 216 to the tube 104 and the pump 110.

The second opening 300 and the second conduit 302 may allow a substantially constant rate of airflow into the manifold layer 204, for example at a leak rate of less than two milliliters per minute when the pressure in the manifold layer 204 is around 80 mmHg. The leak rate through the second opening 300 may be low enough that the pump 110 may need not run constantly to maintain the pressure in the manifold layer 204 with an acceptable range of a desired negative pressure (e.g., a pressure setpoint). Instead, the second opening 300 and the second conduit 302 may be configured to allow a leak rate that allows the pump 110 to be turned off until the pressure deviates from the desired negative pressure by more than a preset limit. To maintain the desired negative pressure in the dressing 102 of FIG. 3, the pump 110 may thus be periodically turned on for limited intervals to reestablish the desired negative pressure. The second opening 300 and the second conduit 302 may be chosen such that a consistent duration of time between periodic operations of the pump 110 may be known or predicted.

Figure 6:
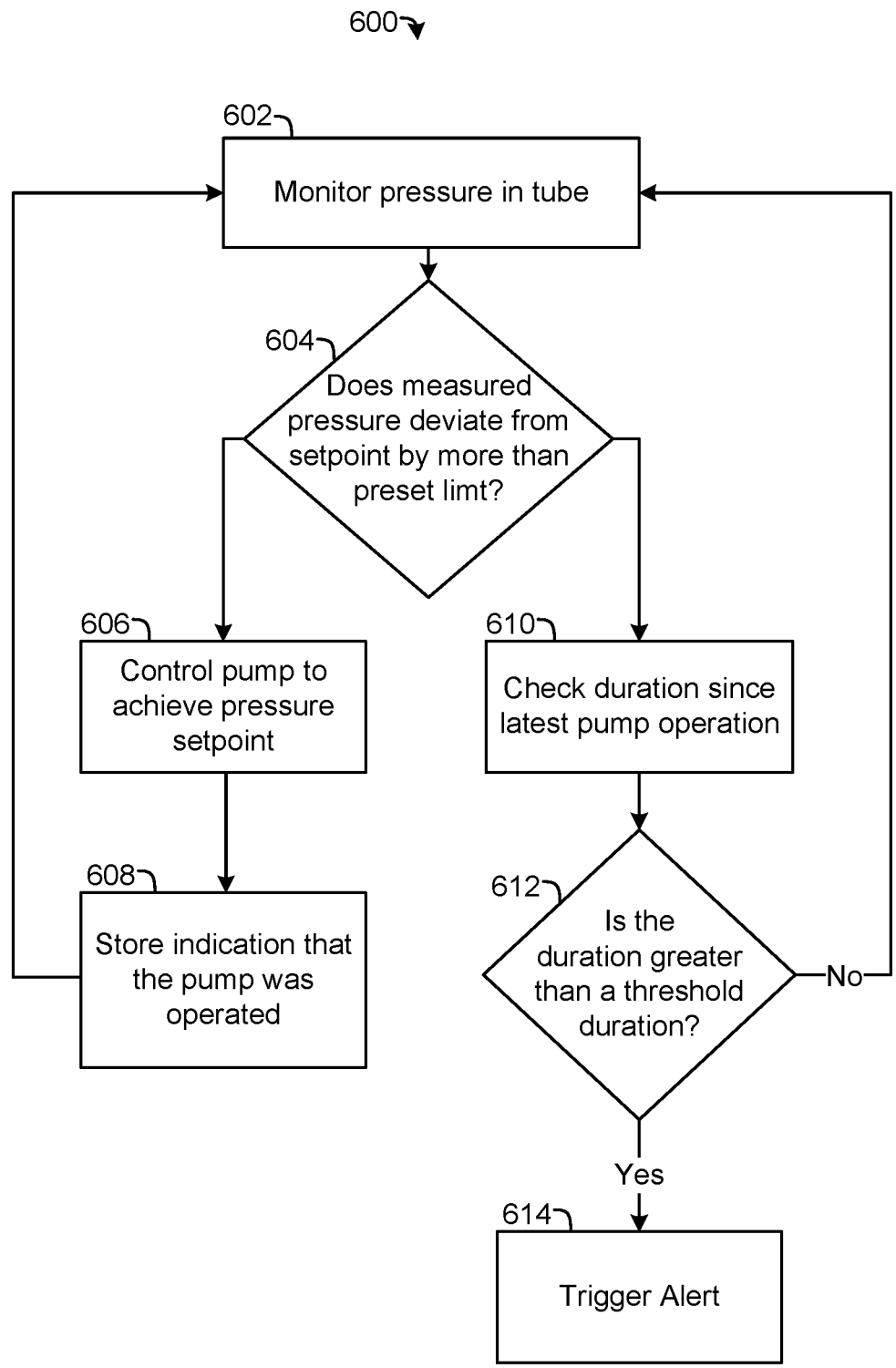
FIG. 6 is a flowchart of a method for full dressing detection for use with the dressings of FIGS. 3-5, according to an exemplary embodiment.

The absorbent layer 206 swells when the absorbent layer 206 absorbs fluid, for example expanding into the second conduit 302 and/or the first conduit 214. Airflow through the second conduit 302 and/or the first conduit 214 is therefore restricted as the absorbent layer 206 absorbs fluid, and may be completely or substantially prevented when the absorbent layer 206 absorbs a threshold amount of fluid (e.g., when the absorbent layer 206 is full). That is, the absorbent layer 206 is configured to swell to block airflow from the second opening 300 to the manifold layer 204, the first opening 210, and the tube 104 when the absorbent layer 206 is full of fluid. When the absorbent layer 206 is full of fluid, then, the leak rate through the second opening 300 is substantially zero. The pump 110 may therefore need not run as frequently to maintain a desired pressure in the manifold layer 204. As shown in FIG. 6 and described in detail with reference thereto, the decrease or elimination of the leak rate through the second opening 300 to the manifold layer 204 may thus be used by the therapy unit 106 to determine that the absorbent layer 206 is full.

Figure 4:
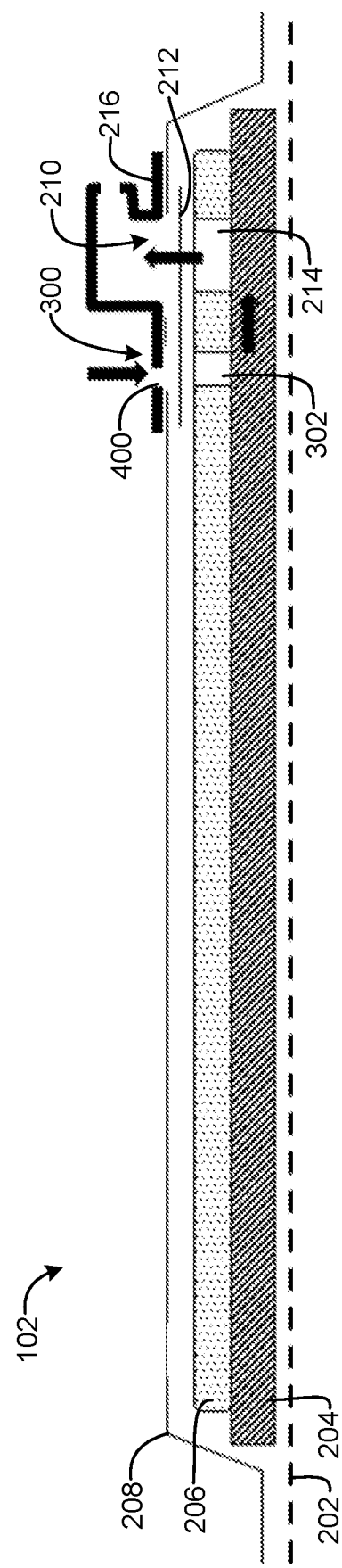
FIG. 4 is an illustration of a third dressing for use with the negative pressure wound therapy system of FIG. 1, according to an exemplary embodiment.

Referring now to FIG. 4, another exemplary embodiment of the dressing 102 is shown. As in FIG. 3, the dressing 102 includes a perforated silicone layer 202, a manifold layer 204 positioned along the perforated silicone layer 202, an absorbent layer 206 positioned along the manifold layer 204, and a drape 208 positioned along the absorbent layer 206. A first opening 210 extends through the drape 208 and is aligned with a first conduit 214. A filter 212 is positioned between the first opening 210 and the first conduit 214, and a connection pad 216 is positioned at the first opening 210 to couple the tube 104 to the drape 208 in pneumatic communication with the first opening 210, the first conduit 214 and the manifold layer 204. A second opening 300 extends through the drape 208 and is aligned with a second conduit 302.

In the embodiment of FIG. 4, the second opening 300 and the second conduit 302 are positioned proximate the first opening 210. The second opening 300 is aligned with a channel 400 that extends through a portion of the connection pad 216. The filter 212, in addition to being positioned between the first opening 210 and the first conduit 214, is also positioned between the second opening 300 and the second conduit 302. Thus, as illustrated in FIG. 4, air may flow into the manifold layer 204 through the channel 400, the second opening 300, the filter 212, and the second conduit 302 at a consistent/predictable leak rate when the absorbent layer 206 is not full of fluid. Air may also out of the manifold layer 204 to the tube 104 via the first conduit 214, the filter 212, the first opening 210, and the connection pad 216, for example when the pump 110 is operating.

As described with reference to FIG. 3, the absorbent layer 206 swells when the absorbent layer 206 absorbs fluid and restricts the airflow from the second opening 300 to the tube 104. When the absorbent layer 206 absorbs a threshold amount of fluid, the leak rate of air through the second opening 300 to the manifold layer 204 and/or to the tube 104 is substantially eliminated and the pump 110 need not run as often to maintain a desired pressure in the tube 104. As described in detail with reference to FIG. 6, the dressing 102 thereby facilitates a determination that the absorbent layer 206 is full.

Figure 5:
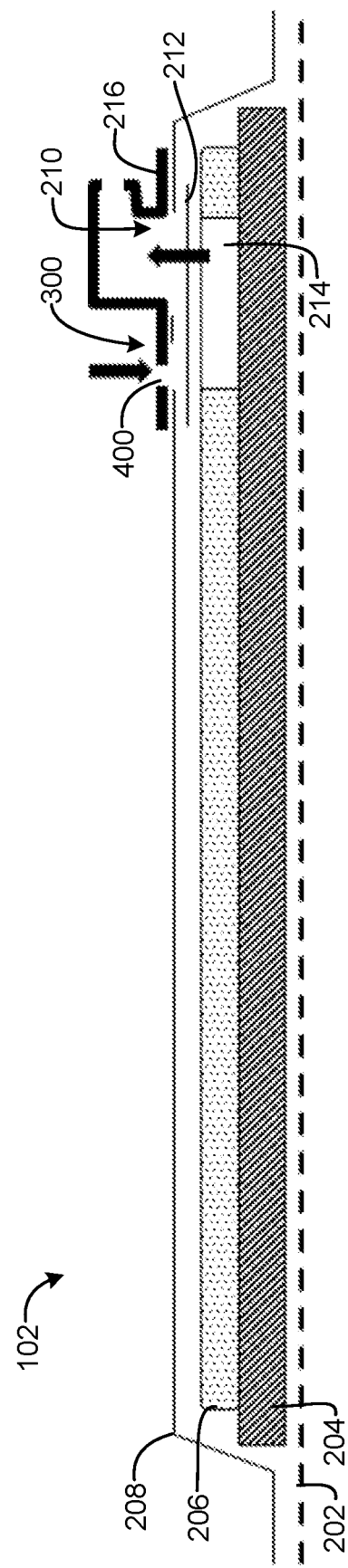
FIG. 5 is an illustration of a fourth dressing for use with the negative pressure wound therapy system of FIG. 1, according to an exemplary embodiment.

Referring now to FIG. 5, another exemplary embodiment of the dressing 102 is shown. As in FIG. 4, the dressing 102 includes a perforated silicone layer 202, a manifold layer 204 positioned along the perforated silicone layer 202, an absorbent layer 206 positioned along the manifold layer 204, and a drape 208 positioned along the absorbent layer 206. A first opening 210 extends through the drape 208 and is aligned with a first conduit 214. A filter 212 is positioned between the first opening 210 and the first conduit 214, and a connection pad 216 is positioned at the first opening 210 to couple the tube 104 to the drape 208 in pneumatic communication with the first opening 210, the first conduit 214 and the manifold layer 204. A second opening 300 extends through the drape 208 and is aligned with a channel 400 through the connection pad 216.

In the embodiment of FIG. 5, the second opening 300 is aligned with the first conduit 214. That is, the first conduit 214 is sized, shaped, and positioned such that both the first opening 210 and the second opening 300 are pneumatically communicable with the first conduit 214. The filter 212 is positioned between the first conduit 214 and the second opening 300 as well as between the first conduit 214 and the first opening 210. Air may flow from the second opening 300 through the first conduit 214 to the manifold layer 204 at a consistent and/or predictable flow rate. Air may also flow from the manifold layer 204 through the first conduit 214 to the tube 104 via the connection pad 216.

When the absorbent layer 206 absorbs fluid, the absorbent layer 206 swells, for example by expanding to block airflow through part or all of the first conduit 214. The absorbent layer 206 swells to block airflow from the second opening 300 to the tube 104 when the absorbent layer 206 is full of fluid. As described in detail below with reference to FIG. 6, the therapy unit 106 may use the loss of airflow through the second opening 300 to determine that the absorbent layer 206 is full.

Referring now to FIG. 6, a process 600 for determining when the dressing 102 is full is shown, according to an exemplary embodiment. The process 600 can be carried out by the control circuit 114 in communication with the pressure sensor 112, the pump 110, and the output device 116 of the therapy unit 106, while the embodiments of dressing 102 shown in FIGS. 3-5 facilitate process 600.

Process 600 begins at step 602, where the control circuit 114 monitors the pressure in the tube 104. The control circuit 114 receives air pressure measurements from the pressure sensor 112. The pressure sensor 112 may continuously measure air pressure or may periodically measure air pressure in the tube 104, for example at set intervals or when prompted for an air pressure measurement by the control circuit 114. The pressure sensor 112 provides the air pressure measurements to the control circuit 114.

At step 604, the control circuit 114 determines whether the pressure (i.e., as indicated by the air pressure measurement from pressure sensor 112) deviates from a pressure setpoint (i.e., a desired pressure) by more than a preset limit. That is, the control circuit 114 compares the measured air pressure to the pressure setpoint and checks whether the difference between the air pressure measurement and the pressure setpoint is greater than the preset limit. In another formulation, the control circuit 114 may check whether the measured air pressure is included in a set of acceptable air pressures (e.g., within a deadband around the pressure setpoint). Because of airflow from the environment to the manifold layer 204 through the second opening 300 at a consistent/predictable leak rate, the measured air pressure may drift from the pressure setpoint to deviate from the pressure setpoint by more than the preset limit in a substantially consistent and/or predictable amount of time. When the absorbent layer 206 is full and airflow from the second opening 300 to the tube 104 is blocked, the measured air pressure may be prevented from drifting from the pressure setpoint to beyond the present limit in the consistent/predicted amount of time.

If the measured air pressure deviates from the pressure setpoint by more than the preset limit, at step 606 the control circuit 114 generates a control signal that causes the pump 110 to operate to achieve the pressure setpoint. That is, the control circuit 114 generates a control signal that causes the pump 110 to turn on and operate to pump air out of the tube 104. The control circuit 114 continues to receive pressure measurements from the pressure sensor 112, and may use the pressure measurements to determine when the air pressure has reached a goal pressure (e.g., the pressure setpoint, a pressure slightly beyond than the pressure setpoint). The control circuit 114 may then generate a control signal to turn off the pump 110 when the air pressure reaches the goal pressure.

At step 608, the control circuit 114 stores an indication that the pump 110 was turned on. The indication that the pump 110 was operated indicates when the pump 110 was operated. In some embodiments, the control circuit 114 stores a log of pump operations that includes a time stamp that indicates when the pump 110 was operated (e.g., a record of the latest operation of the pump 110, a log of all operations of the pump 110). In other embodiments, the control circuit 114 stores an indication that the pump 110 was operated by restarting a timer that measures a duration since the preceding operation of the pump 110. In various embodiments, the control circuit 114 may store any type of indication that allows the control circuit 114 to determine a duration of time since the preceding operation of the pump 110. The process 600 then returns to step 602 where the control circuit 114 and the pressure sensor 112 continue to monitor the pressure in the tube 104.

If, at step 604, the control circuit 114 determines that the pressure does not deviate from the pressure setpoint by more than the preset limit, the process 600 moves on to step 610. At step 610, the control circuit 114 determines the duration of time since the latest operation of the pump 110 (i.e., the immediately preceding instance of the pump 110 being turned on). The control circuit 114 determines the duration based on an indication that the pump 110 was turned on (e.g., as stored at step 608 and discussed above), for example by reading the duration from a timer or by comparing the current time to the time indicated by a time stamp in a log of pump operations.

At step 612, the control circuit 114 checks whether the duration since the latest pump operation is greater than a threshold duration. The threshold duration may correspond to an expected or predicted amount of time required for the air pressure in the manifold layer 204 to drift away from the pressure setpoint beyond a preset limit due to airflow into the manifold layer 204 through the second opening 300 and the second conduit 302. When the absorbent layer 206 absorbs fluid and swells, the second conduit 302 is blocked and the leak rate of air through the second conduit 302 is decreased or eliminated, which increases the amount of time required for the pressure measured by pressure sensor 112 to drift away from the pressure setpoint (i.e., drift towards atmospheric pressure due to leaks). In such a case, a duration since the latest pump operation that exceeds the threshold duration indicates that the second conduit 302 is blocked, and thus that the absorbent layer 206 is swollen and full of fluid. The threshold duration may be set at or close to the expected or predicted amount of time required for the air pressure in the manifold layer 204 to drift away from the pressure setpoint beyond a preset limit to identify full dressings as soon as possible, or may be set significantly longer than that amount of time to prevent false positive full dressing determinations. The threshold duration may be preset by a manufacturer, input by a patient or caregiver, or automatically determined by the control circuit 114 based on historical data.

If the control circuit 114 determines that the duration since the latest operation of pump 110 exceeds the threshold duration, the control circuit 114 triggers an alert. The control circuit 114 transmits a signal indicating that the dressing 102 is full to the output device 116. According to various embodiments, the output device 116 may, in response to the signal indicating that the dressing 102 is full, cause one or more lights to turn on, turn off, change colors, blink, etc., cause one or more speakers to play a sound (e.g., alarm, ring, beep, vocal recording), display a message stating that the dressing 102 is full, transmit a message via a network to a user electronic device or provider computer system, and/or generate an alert that informs a user that the dressing 102 is full in some other way. The therapy unit 106 thereby informs a user that the dressing 102 is full and should be replaced.

If the control circuit 114 determines that the duration since the latest pump operation is less than the threshold duration at step 612, then the process 600 returns to step 602 where the control circuit 114 continues to monitor pressure in the tube 104. Process 600 may run periodically (e.g., every second, every five minutes, every thirty minutes) until a determination is made that the dressing 102 is full and an alert is triggered at step 614.

Dressing with Sensing Port for Full Dressing Detection

Figure 7:
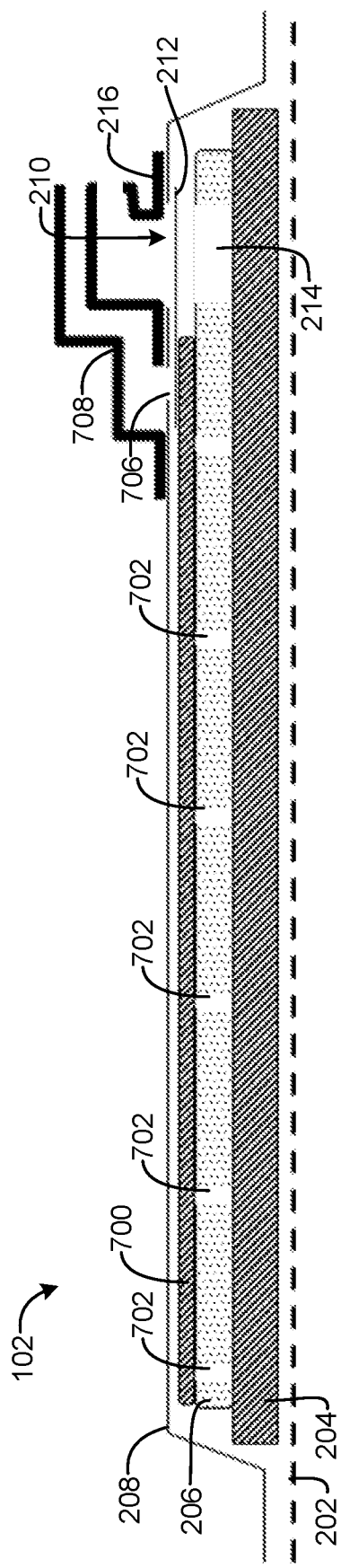
FIG. 7 is an illustration of a fifth dressing for use with the negative pressure wound therapy system of FIG. 1, according to an exemplary embodiment.

Referring now to FIG. 7, another embodiment of the dressing 102 is shown. As in FIGS. 2-5, the dressing 102 of FIG. 7 includes a perforated silicone layer 202, a manifold layer 204 positioned along the perforated silicone layer 202, an absorbent layer 206 positioned along the manifold layer 204, and a drape 208. A first opening 210 extends through the drape 208 and is aligned with a first conduit 214. A filter 212 is positioned between the first opening 210 and the first conduit 214, and a connection pad 216 is positioned at the first opening 210 to couple the tube 104 to the drape 208 in pneumatic communication with the first opening 210, the first conduit 214 and the manifold layer 204.

The dressing 102 of FIG. 7 also includes a second manifold layer 700 positioned between the absorbent layer 206 and the drape 208. The second manifold layer 700 is made of a similar or identical material as the first manifold layer 204. Accordingly, the second manifold layer 700 allows airflow therethrough and maintain a substantially constant volume even under negative pressure. The second manifold layer 700 is positioned abutting the absorbent layer 206.

In the embodiment of FIG. 7, the absorbent layer 206 includes a plurality of perforations 702. The perforations may be 2-4 mm in diameter and may be spaced evenly on the absorbent layer 206. The perforations 702 allow air to flow from the manifold layer 204 to the second manifold layer 700, such that the air pressure in the manifold layer 204 is substantially equivalent to the air pressure in the second manifold layer 700. The dressing 102 may be configured such that the only path for airflow from the second manifold layer 700 to the tube 104 is via the perforations 702, the manifold layer 204, and the first conduit 214.

When the absorbent layer 206 absorbs fluid, the absorbent layer 206 swells and restricts the perforations 702. When the absorbent layer 206 is full of fluid, the perforations 702 are closed by the swelling of the absorbent layer 206 and airflow between the manifold layer 204 and the second manifold layer 700 is prevented. In such a case, airflow between the second manifold layer 700 and the tube 104 is prevented.

As shown in FIG. 7, the dressing 102 includes a second opening 706 that extends through the drape 208 and is aligned with the second manifold layer 700. A sensing port 708 is coupled to the drape 208 in pneumatic communication with the second opening 706 and the second manifold layer 700. The sensing port 708 facilitates a measurement of the air pressure of the second manifold layer 700. For example, the sensing port 708 may be pneumatically communicable with the therapy unit 106 via a second tube. In such a case, a pressure sensor 112 measures the pressure in the second tube, effectively measuring the air pressure of the second manifold layer 700. As shown in FIG. 7, the sensing port 708 is included as part of the connection pad 216 (e.g., coupled to the connection pad 216, formed integrally with the connection pad 216). In other embodiments, the sensing port 708 is separate from the connection pad 216, such that the sensing port 708 and the second opening 706 may be positioned anywhere on the drape 208.

The connection pad 216 and the sensing port 708 thereby allow independent pressure measurements of the manifold layer 204 and the second manifold layer 700, respectively. When the perforations 702 are open (i.e., when the absorbent layer 206 is not full), airflow between the manifold layer 204 and the second manifold layer 700 ensures that the air pressure remains substantially equivalent in the manifold layer 204 and the second manifold layer 700. However, when the absorbent layer 206 is full and the perforations 702 are closed to prevent airflow between the manifold layer 204 and the second manifold layer 700, the air pressure in the manifold layer 204 may diverge from the air pressure in the second manifold layer 700. This divergence may be exacerbated by operation of the pump 110 to pump air out of the manifold layer 204 via the connection pad 216 and the tube 104. Thus, a difference between the pressure measured at the sensing port 708 (i.e., the pressure of the second manifold layer 700) and the pressure measured at the connection pad 216 (i.e., the pressure of the manifold layer 204) indicates that the perforations 702 are closed and, accordingly, that the absorbent layer 206 is full of fluid.

Figure 8:
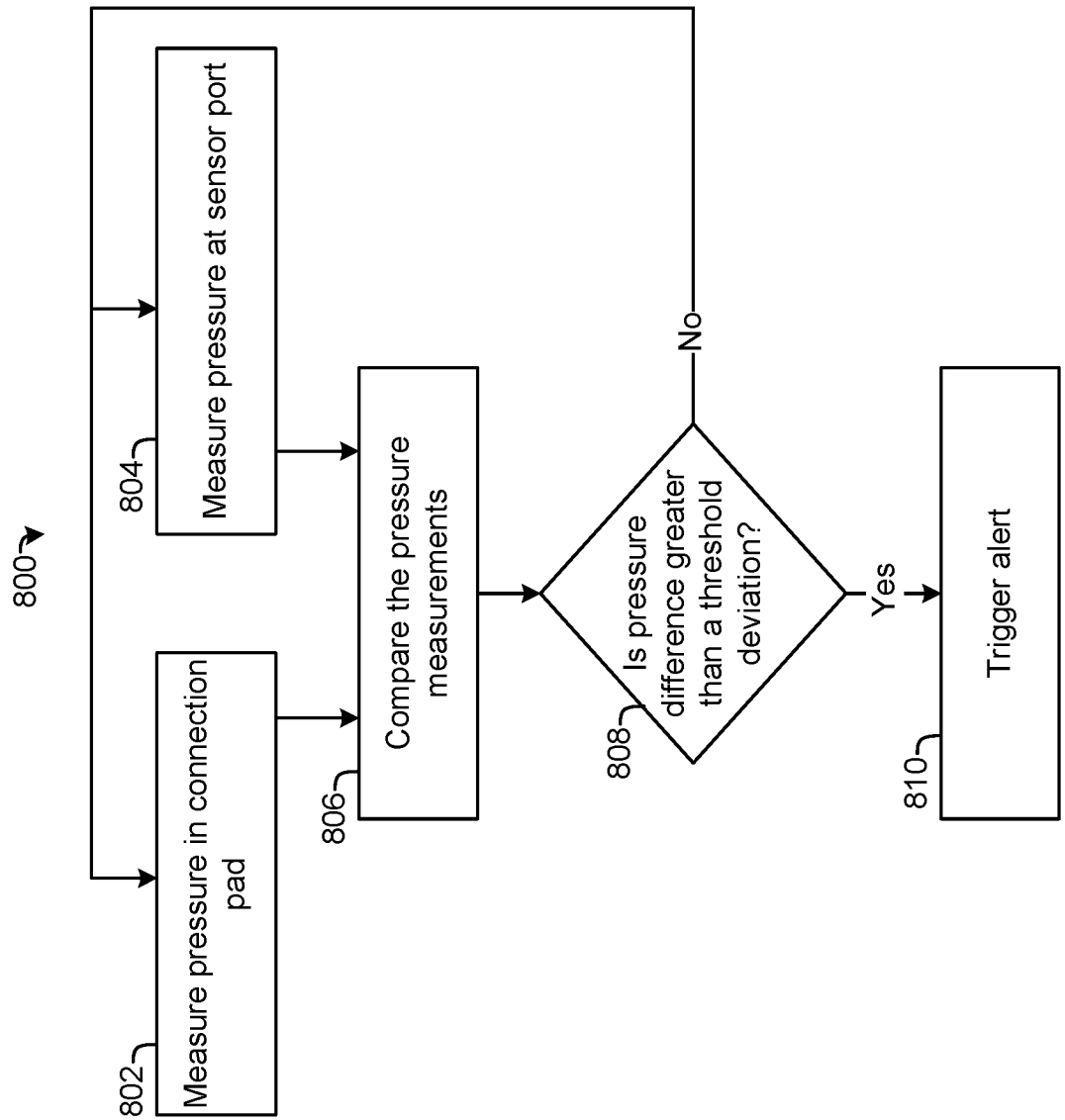
FIG. 8 is a flowchart of a method for full dressing detection in the dressing of FIG. 7, according to an exemplary embodiment.

Referring now to FIG. 8, a process 800 for detecting that the dressing 102 is full is shown, according to an exemplary embodiment. The process 800 can be executed by the control circuit 114 of the therapy unit 106. The process 800 is particularly suited for use with the embodiment of dressing 102 shown in FIG. 7.

Process 800 begins at step 802, where air pressure at the connection pad 216 is measured, and at step 804, where air pressure at the sensing port 708 is measured. At step 802, the pressure sensor 112 measures air pressure in the tube 104 that is pneumatically communicable with the pump 110, the connection pad 216, the first opening 210, and the manifold layer 204. The pressure measured at step 802 is therefore effectively the air pressure of the manifold layer 204. At step 804, a pressure sensor measures air pressure in a sensor tube that is pneumatically communicable with the sensing port 708, the second opening 706, and the second manifold layer 700. The pressure measured at step 804 is therefore effectively the air pressure of the second manifold layer 700. The pressure measurements are provided to the control circuit 114. Steps 802 and 804 are executed simultaneously or substantially simultaneous, such that contemporaneous measurements of the air pressure in the manifold layer 204 and of the air pressure in the second manifold layer 700 are received by the control circuit 114.

At step 806, the control circuit 114 compares the pressure at the connection pad 216 to the air pressure at the sensing port 708. That is, the control circuit 114 compares the pressure of the manifold layer 204 to the pressure of the sensing port 708. The control circuit 114 determines the pressure difference between the pressure measurements by subtracting the pressure of the manifold layer 204 from the pressure of the sensing port 708 or vice versa. Because the pressure measurements are contemporaneous, the pressure difference represents the difference between the two pressure measurements at a particular moment in time.

At 808, the control circuit 114 determines whether the pressure difference is greater than a threshold deviation. When the perforations 702 are open and air flows between the between the manifold layer 204 and the second manifold layer 700, the pressure difference will be zero or close to zero, and less than the threshold deviation. When the absorbent layer 206 is full of fluid and swells to close the perforations 702, however, the lack of airflow between the manifold layer 204 and the second manifold layer 700 allows the pressure difference to increase. Thus, a pressure difference greater than the threshold deviation indicates that airflow between the manifold layer 204 and the second manifold layer 700 is blocked, and, accordingly, that the absorbent layer 206 is full of fluid.

If the control circuit 114 determines that the pressure difference is less than the threshold deviation, the process 800 returns to step 802 and step 804 to take new pressure measurements. Steps 802-808 may be repeated on a regular schedule (e.g., every ten minutes, every thirty minutes, every hour) and/or may be executed in response to a request from a user.

If the control circuit 114 determines that the pressure difference is greater than the threshold deviation, at step 810 the control circuit 114 triggers an alert to inform a patient and/or caregiver that the dressing 102 is full and should be replaced. In some embodiments, the control circuit 114 repeats steps 802-808 one or more times to verify that the dressing 102 is full before triggering the alert. To trigger the alert, the control circuit 114 provides an indication that the dressing 102 is full to the output device 116. According to various embodiments, the output device 116 may, in response to the signal indicating that the dressing 102 is full, cause one or more lights to turn on, turn off, change colors, blink, etc., cause one or more speakers to play a sound (e.g., alarm, ring, beep, vocal recording), display a message stating that the dressing 102 is full, transmit a message via a network to a user electronic device or provider computer system, and/or generate an alert that informs a user that the dressing 102 is full in some other way. The therapy unit 106 thereby informs a user that the dressing 102 is full and should be replaced.

Full Dressing Detection Based on Pump Noise Response

Figure 9:
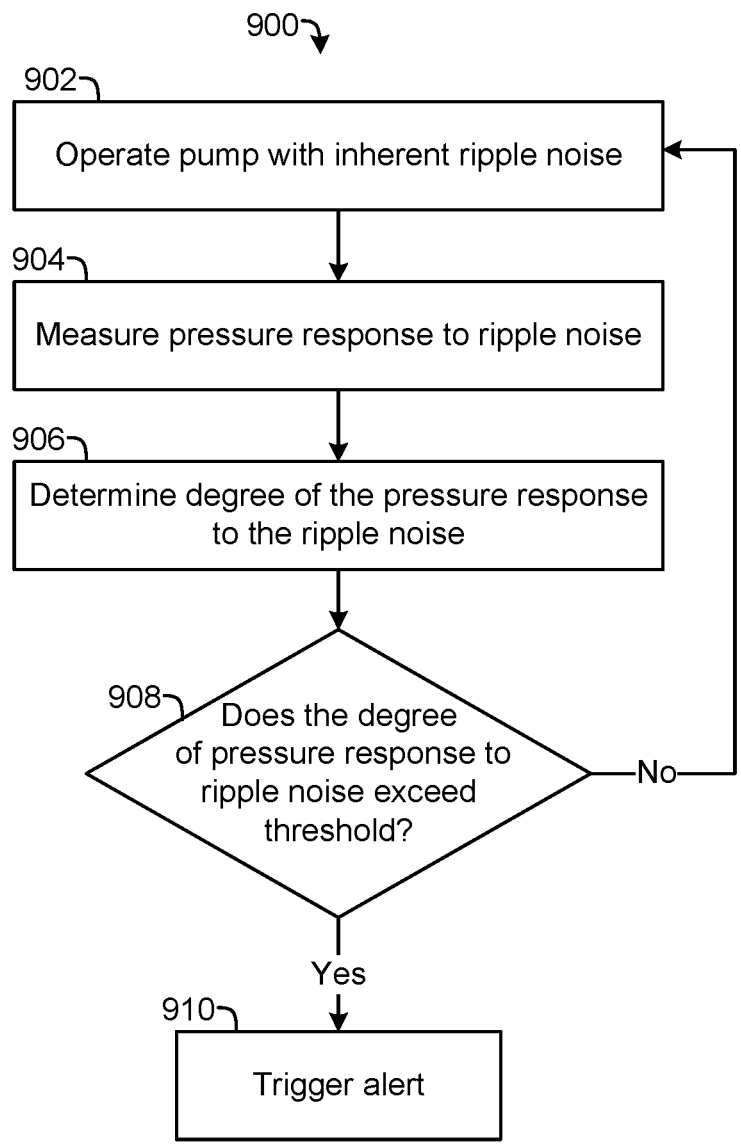
FIG. 9 is a flowchart of a method for full dressing detection with the negative pressure wound therapy system of FIG. 1, according to an exemplary embodiment.
Figure 10:
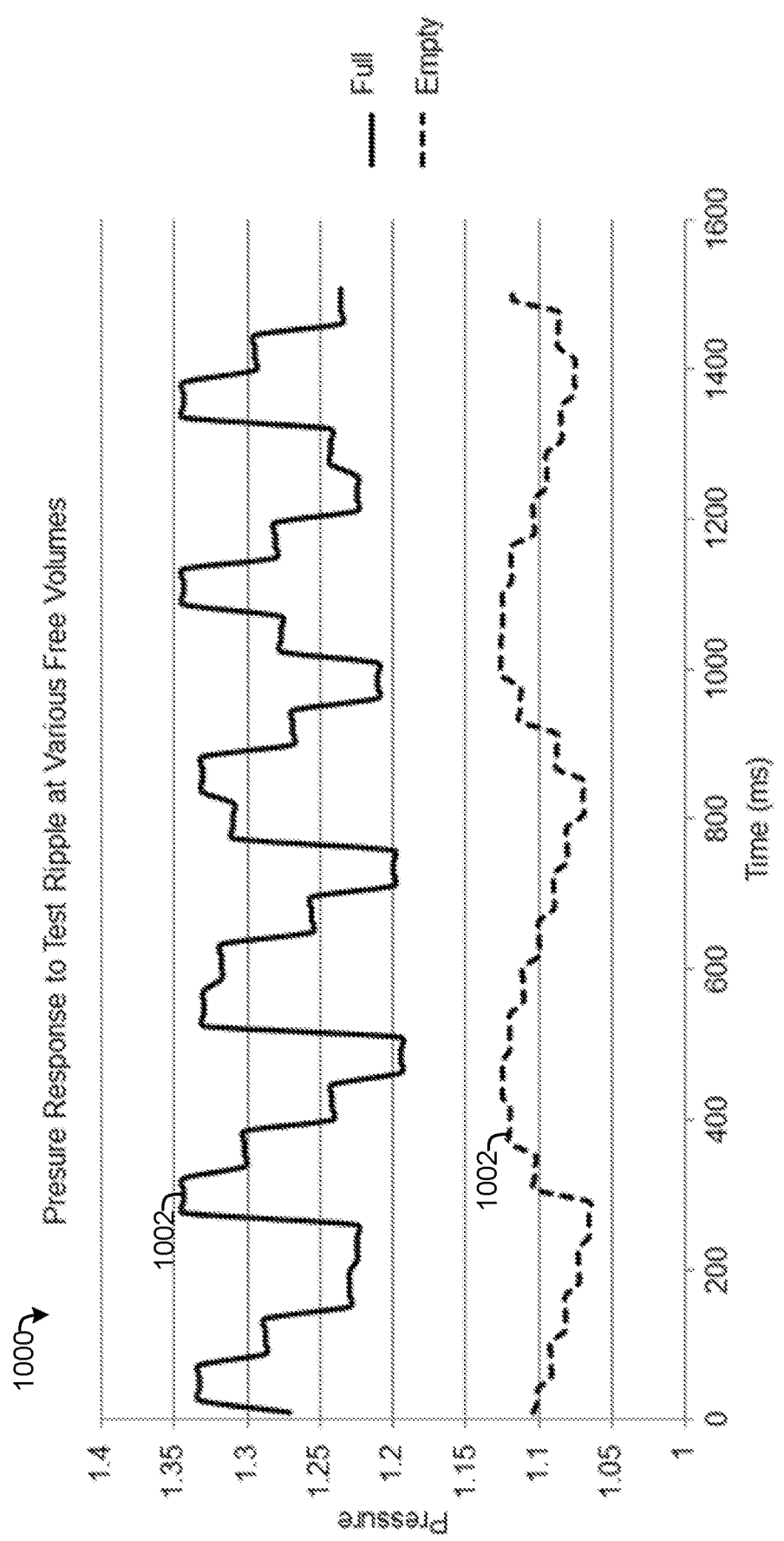
FIG. 10 is a graph of pressure responses that illustrate the method of FIG. 9, according to an exemplary embodiment.

Referring now to FIGS. 9-10, a process 900 for detecting that the dressing 102 is full based on a pressure response to pump noise is illustrated, according to an exemplary embodiment. FIG. 9 shows a flowchart of the process 900, while FIG. 10 shows a graph 1000 useful for explaining process 900. Process 900 may be carried out by the NPWT system 100, and more particularly by the therapy unit 106 coupled via tube 104 to dressing 102. Process 900 is suitable for use with any of the embodiments of dressing 102 described herein, for example dressing 102 as shown in FIG. 2.

At step 902, the pump 110 is operated with an inherent noise ripple to pump air out of the dressing 102. The physical structure of pump 110 causes the rate of air pumped through the pump 110 to vary with a noise ripple, even as the pump 110 operates at a constant power. For example, the pump 110 may be a positive displacement pump such as a diaphragm pump that has a cyclical operation that causes noise in the rate of air pumped through the pump 110. This noise may have a repeating pattern, and thus be characterized as a noise ripple. In some embodiments, the drive frequency of the pump is altered to accentuate the noise. For example, the control circuit 114 may periodically (e.g., every ten minutes, every thirty minutes) generate a control signal that alters the drive frequency of the pump to a drive frequency at which the pump generates a particularly large amount of noise.

At step 904, the pressure sensor 112 measures the pressure in the tube 104, and thus the pressure response to the noise ripple. The pressure sensor 112 may continuously measure the pressure in the tube 104 or make repeated measurements. The pressure sensor 112 provides the pressure measurements to the control circuit 114. The control circuit 114 collects the pressure measurements in a pressure data time series, from which the pressure response to the noise ripple overtime can be identified.

FIG. 10 shows a graph 1000 of two pressure data time series as collected at step 904. Line 1002 graphs the pressure response to the noise ripple for a full dressing 102, while line 1004 graphs the pressure response to the noise ripple for an empty dressing 102. When the dressing 102 is empty, a larger volume of air is available in the dressing 102 to dampen the pressure response to the test ripple, such that the noise has less effect on the pressure measured by the pressure sensor 112 (as illustrated by line 1004). When the dressing 102 is full, a smaller volume of air is available at the dressing 102 to dampen the pressure response to the test ripple, such that the noise has a more significant effect on the pressure measured by the pressure sensor 112 (as illustrated by line 1002). Thus, a more significant pressure response to the noise ripple corresponds to a higher level of fluid in the dressing 102.

At step 906, the control circuit 114 determines the degree of the pressure response to the noise ripple. The degree of the pressure response may correspond to an amplitude of the pressure response, a slope of the pressure response, and/or some other information that quantifies the extent to which the measured pressure responds to the noise ripple. At step 908, the control circuit 114 determines whether the degree of the pressure response to the noise ripple exceeds a limit. The limit represents a degree beyond which the pressure response indicates that the dressing 102 is full. In some embodiments, the control circuit 114 may associate the degree of the pressure response with a fill level of the dressing 102, such that the therapy unit 106 may provide a user with more information about the status of the dressing 102 beyond a dichotomous full or not full determination.

If, at step 908, the control circuit 114 determines that the degree of pressure response to the noise ripple does not exceed the limit, the process 900 repeats steps 902-908. Steps 902-908 may be repeated at may be repeated on a regular schedule (e.g., every ten minutes, every thirty minutes, every hour) and/or may be executed in response to a request from a user.

If the control circuit 114 determines that the degree of pressure response to the noise ripple exceeds the limit, at step 910 the control circuit 114 triggers an alert to inform a patient and/or caregiver that the dressing 102 is full and should be replaced. In some embodiments, the control circuit 114 repeats steps 902-908 one or more times to verify that the dressing 102 is full before triggering the alert (e.g., repeating steps 902-908 several times over an hour or half of an hour). In some cases, it may be possible for the fluid to evaporate from the dressing such that the dressing 102 is no longer full and the alert need not be triggered. To trigger the alert, the control circuit 114 provides an indication that the dressing 102 is full to the output device 116. According to various embodiments, the output device 116 may, in response to the signal indicating that the dressing 102 is full, cause one or more lights to turn on, turn off, change colors, blink, etc., cause one or more speakers to play a sound (e.g., alarm, ring, beep, vocal recording), display a message stating that the dressing 102 is full, transmit a message via a network to a user electronic device or provider computer system, and/or generate an alert that informs a user that the dressing 102 is full in some other way. The therapy unit 106 thereby informs a user that the dressing 102 is full and should be replaced.

Configuration of Exemplary Embodiments

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

It should be noted that the orientation of various elements may differ according to other exemplary embodiments and that such variations are intended to be encompassed by the present disclosure.

It is important to note that the constructions and arrangements of the NPWT system 100 as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

What is claimed is:

1. A dressing, comprising:
   a drape sealable over a wound bed;
   an absorbent layer coupled to the drape and configured to absorb fluid from the wound bed;
   a manifold layer abutting the absorbent layer, the manifold layer allowing the flow of air and fluid therethrough, the absorbent layer positioned between the manifold layer and the drape;
   a first opening extending through the drape;
   a first conduit extending though the absorbent layer and pneumatically communicable with the first opening and the manifold layer;
   a first filter positioned between the first opening and the first conduit;
   a connection pad positioned on the drape at the first opening, the connection pad configured to couple a tube to the dressing in pneumatic communication with the first opening, the tube coupled to a pump that provides a negative pressure to the wound bed; and
   a second opening extending through the drape that allows an airflow from the second opening to the tube via the manifold layer;
   wherein the absorbent layer is configured to swell to block the airflow from the second opening to the tube when the absorbent layer is full of fluid.

2. The dressing of claim 1, wherein the pump is configured to detect that the absorbent layer is full of fluid by determining that the airflow from the second opening to the tube is blocked.

3. The dressing of claim 1, further comprising a second conduit extending through the absorbent layer and pneumatically communicable with the second opening and the manifold layer.

4. The dressing of claim 3, further comprising a second filter positioned between the second opening and the second conduit.

5. The dressing of claim 3, wherein the first filter is positioned between the second opening and the second conduit.

6. The dressing of claim 1, wherein the second opening is aligned with a channel extending through the connection pad.

7. The dressing of claim 1, wherein the second opening is aligned with the first conduit and the first filter.

8. The dressing of claim 1, further comprising a perforated silicon layer abutting the manifold layer.

* * * * *

UNITED STATES PATENT AND TRADEMARK OFFICE
CERTIFICATE OF CORRECTION

| | | |
|---|---|---|
| PATENT NO. | : 11,224,543 B2 | Page 1 of 1 |
| APPLICATION NO. | : 16/393437 | |
| DATED | : January 18, 2022 | |
| INVENTOR(S) | : Christopher Brain Locke | |

It is certified that error appears in the above-identified patent and that said Letters Patent is hereby corrected as shown below:

In the Claims

<u>Column 18</u>
Line 1, In Claim 1, delete "though", and insert -- through --, therefor.

Signed and Sealed this
Ninth Day of April, 2024

*Katherine Kelly Vidal*

Katherine Kelly Vidal
*Director of the United States Patent and Trademark Office*